US006838244B1

(12) United States Patent
Li et al.

(10) Patent No.: US 6,838,244 B1
(45) Date of Patent: Jan. 4, 2005

(54) FLUORESCENT OLIGONUCLEOTIDES AND USES THEREOF

(75) Inventors: Wan-Liang Robert Li, Valley Park, MO (US); Jian S. Zhou, Alpharetta, GA (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 09/859,736

(22) Filed: May 18, 2001

Related U.S. Application Data (60) Provisional application No. 60/205,452, filed on May 19, 2000.

(51) Int. Cl.[7] .......................... C12Q 1/68; C12P 19/34; C07H 21/02; C07H 21/04; C07H 19/00
(52) U.S. Cl. ........................ 435/6; 435/91.1; 435/91.2; 435/91.21; 536/221; 536/23.1; 536/24.3; 536/24.31; 536/24.32; 536/24.33; 536/25.3; 422/50; 422/52; 422/56; 422/55; 422/57; 702/20
(58) Field of Search ........................ 435/6, 91.1, 91.2, 435/91.51; 536/22.1, 23.1, 24.3, 24.33, 25.3, 25.32, 26.6; 422/50, 52, 56, 55, 57; 702/20

(56) References Cited

U.S. PATENT DOCUMENTS

| | | | | |
|---|---|---|---|---|
| 4,458,066 A | | 7/1984 | Caruthers et al. | 536/27 |
| 5,804,386 A | * | 9/1998 | Ju | 435/10 |
| 5,830,658 A | * | 11/1998 | Gryaznov | 435/6 |
| 5,853,992 A | * | 12/1998 | Glazer et al. | 435/6 |
| 6,060,240 A | * | 5/2000 | Kamb et al. | 435/6 |
| 2002/0051981 A1 | * | 5/2002 | Getts | 435/6 |

OTHER PUBLICATIONS

1998 Qiagen catalog (pp. 7–8).*
Stears et al., "A novel, sensitive detection system for high–density microarrays using dendrimer technology", *Physical Genomics*, 3:93–99 (2000).
Beaucage, S.L., et al., "Deoxynucleoside Phosphoramidities–A New Class of Key Intermediates for Deoxypolynucleotide Synthesis", *Tetrahedron Letters*, 22:1859–1962, (1981).
DeRisi, J.L., et al., "Exploring the Metabolic and Genetic Control of Gene Expression on a Genomic Scale", *Science*, 278:680–686, (1997).
Heller, R.A., et al., "Discovery and Analysis of Inflammatory Disease–Related Genes Using cDNA Microarrays", *Proc. Natl. Acad. Sci. USA*, 94:2150–2155, (1997).
Liang, P., et al., "Differential Display of Eukaryotic Messenger RNA by Means of the Polymerase Chain Reaction", *Science*, 257:967–971, (1992).
Matteucci, M.D., et al., "Synthesis of Deoxyoligonucleotides on a Polymer Support" *J. Am. Chem. Soc.*, 103:3185–3191, (1981).
Prober, J.M., et al., "A System for Rapid DNA Sequencing with Fluorescent Chain–Terminating Dideoxynucleotides" *Science*, 238:336–341, (1987).

(List continued on next page.)

*Primary Examiner*—Jeffrey Siew
(74) *Attorney, Agent, or Firm*—Thomas E. Kelley; Lawrence M. Lavin, Jr.; Arnold & Porter LLP (57) ABSTRACT

Oligonucleotide molecules labeled with a plurality of fluorophores of one or more types embedded in the backbone of said oligonucleotide, wherein at least one of said fluorophores is not located at either the 3' or 5' terminus of said oligonucleotide. The invention further provide methods for using the subject labeled oligonucleotides in detecting biological molecules, sequencing DNA molecules and particularly generating cDNA molecules for characterizing the differential expression of genes.

33 Claims, 1 Drawing Sheet

OTHER PUBLICATIONS

Ruan, Y., et al., "Towards Arabidopsis Genome Analysis: Monitoring Expression Profiles of 1400 Genes Using cDNA Microarrays", *The Plant Journal*, 15:821–833 (1998).

Schena, M., et al., "Quantative Monitoring of Gene Expression Patterns with a Complementary DNA Microarray", *Science*, 270:467–470, (1995).

Schena, M., et al., "Parallel Human Genome Analysis: Microarray–based Expression Monitoring of 1000 Genes", *Proc. Natl. Acad. Sci. USA*, 93:10614–10619 (1996).

Smith, L.M., et al., "Fluorescence Detection in Automated DNA Sequence Analysis", *Nature*, 321:674–679, (1986).

Wu, R. (ed.), *"Methods in Enzymology"* 155:51–334, (1987).

* cited by examiner

Figure 1

FLUORESCENT OLIGONUCLEOTIDES AND USES THEREOF

CROSS-REFERENCE TO RELATED APPLICATIONS

This application claims priority under 35 U.S.C § 119(e) of U.S. provisional application Ser. No. 60/205,452 filed on May 19, 2000, the entire content of which is incorporated herein by reference.

INCORPORATION OF SEQUENCE LISTING

A paper copy of the Sequence Listing and a copy of the Sequence Listing on diskette, containing the file named SeqList.txt, which is 2,006 bytes in size (measured in MS-DOS) and created on May 23, 2003, is herein incorporated by reference.

FIELD OF INVENTION

The present invention is generally related to a labeled fluorescent oligonucleotide, methods for using such labeled oligonucleotide in detecting biological molecules, sequencing DNA molecules and generating cDNA molecules for characterizing the differential expression of genes.

BACKGROUND

Gene expression, which is for biological processes such as aging, development, differentiation, metabolite production, progression of the cell cycle, and infectious or genetic or other disease states, can be characterized by determining the level (i.e., the concentration of mRNA in a sample, etc.) or pattern (i.e., the kinetics of expression, rate of decomposition, stability profile, etc.) of the expression of a protein encoded by a gene under study. A variety of methods are currently available for accomplishing this task. One such method is a microarray-based approach (Schena et al., *Science* 270: 467–470 (1995), which is incorporated herein by reference in its entirety). This 'chip'-based approach involves: (1) generating two populations of fluorescently labeled cDNA probes from two MRNA samples which are isolated from two physiological sources, where each population of cDNA probes is labeled with one of two distinct labeled oligonucleotides capable of generating distinguishable fluorescent signals at two wavelengths; (2) simultaneously hybridizing the two populations of fluorescently labeled cDNA probes to gene targets on a microarray; (3) separately detecting intensities of hybridization signals for each of elements on the microarray at two distinguishable wavelengths and determining the hybridization patterns of two samples; and (4) calculating ratios of gene expression levels from two co-hybridized samples. This 'chip'-based technology can allow quantitatively monitoring of differential expression of hundreds and thousands of genes simultaneously (Schena et al., *Proc. Natl. Acad. Sci. USA* 93: 10614–10619 (1996); Heller et al., *Proc. Natl. Acad. Sci. USA* 94: 2150–2155 (1997); DeRisi et al., *Science* 278: 680–686; and Ruan et al., *Plant J.* 15: 821–833 (1998), all of which are incorporated herein by reference in their entirety) and can provide a powerful tool for gene discovery, functional analysis and elucidation of genetic regulatory networks.

Despite the great promise of this 'chip'-based technology, there are still problems with respect to enhancing its reliability and optimizing its performance. For instance, its detection sensitivity still needs to be greatly improved. The detection sensitivity of the microarray technology is mainly limited by the fluorescence emission quantum yield of labeled oligonucleotides for labeling cDNA probes. With currently available labeled oligonucleotides comprising a single fluorophore, hybridization signals for low expressed genes could be so weak that the intrinsic noise of instruments could render ratio measurements unreliable. Without further enhancement in signal-to-noise ratio, current microarray methods probably will be limited to the characterization of differential expression for highly-expressed genes.

One class of labeled oligonucleotides which typically has been developed is energy transfer (ET) fluorescent dyes. Such energy transfer fluorescent dyes include a donor fluorophore and an acceptor fluorophore. In these dyes, when the donor and acceptor fluorophores are positioned in proximity with each other and with the proper orientation relative to each other, the energy emission from the donor fluorophore is absorbed by the acceptor fluorophore and causes the acceptor fluorophore to emit light at a longer wavelength. In these ET labeled oligonucleotides, such energy transfer was exploited to make a set of labels having high absorbance at a common wavelength but well-separated fluorescence emission maximums. However, the fluorescence per ET label molecule was not increased. Such ET labeled oligonucleotides are not suitable for enhancing the detection sensitivity of the microarray technology, since two distinct labeled oligonucleotides can be excited at two distinguishable wavelengths.

Thus, there remains a continuing need for new labeled oligonucleotides which have much higher fluorescence per molecule and could enhance greatly the signal to noise ratio so that differential expression of low expressed genes could be reliably determined.

Furthermore, current methods of fluorescently labeled cDNA preparations are not entirely satisfactory. In current preparation methods, poly A RNA (mRNA) needs to be isolated first from total RNA and then fluorescent cDNA probes are prepared from the isolated mRNA. One problem with current methods is that large amounts of starting materials are required because of potential sample loss during mRNA isolation. Another problem is that the lost amount of a specific MRNA can vary from preparation to preparation from the above two laborious preparation steps. Such preparation-to-preparation variation can artificially introduce apparent differential expression of genes being tested and affect the reliability of the microarray method. Another problem is that current methods can generate fluorescently labeled cDNA probes of short length, for instance, less than about 300 nucleotides. With such short probes, hybridization of the cDNA probes to the targets on microarrays has to be carried out under less stringent conditions so that the reliability of experimental results is compromised. If the length of cDNA probes ranged from 500 to 1200 nucleotides, the hybridization of the fluorescent cDNA probes to the targets on microarrays could be performed under optimal conditions.

Thus, there remains a continuing need for the development of cDNA probe preparation methods wherein the amount of starting materials and artificial errors in ratios of gene expression levels can be minimized, the length of cDNA probes is longer, and the cDNA probes have much higher fluorescence per molecule.

It is an object of the present invention to provide a labeled oligonucleotide which has high fluorescence per molecule and can be used to detect biological molecules with high sensitivity.

It is another object of the invention to provide an oligonucleotide primer which includes the labeled oligonucleotide of the invention.

It is another object of the invention to provide a method for generating, from smaller amount of RNA samples, fluorescently labeled cDNA probes which have a much higher fluorescence per molecule and the length of which is from 500 to 1000 nucleotides.

SUMMARY OF THE INVENTION

The invention provides, in one aspect, a labeled oligonucleotide comprising a plurality of fluorophores of one or more types which are embedded in the backbone of the labeled oligonucleotide.

The invention provides, in another aspect, an oligonucleotide labeled with a plurality of fluorophores of one or more types which are embedded in the backbone of the oligonucleotide, wherein at least one of these fluorophores is not located at either the 3' or 5' terminus of the oligonucleotide.

The invention provides, in another aspect, a labeled oligonucleotide having the structure wherein N is a nucleotide unit; F and F' are respectively a first and a second fluorophores which are covalently attached to the sugar moiety of N through a sugar linkage such that the first and second fluorophores are constituents of a polymeric chain; F and F' can be the identical fluorophores or different fluorophores capable of producing distinguishable fluorescent signals at two distinguishable wavelength; i and j are integers ranging from 2 to 7; s is 0 or 1; and r is an integer ranging from 1 to 5.

The invention provides, in another aspect, a branched labeled oligonucleotide having the structure wherein N is a nucleotide unit; F and F' are respectively a first and a second fluorophore which is covalently attached to the sugar moiety of N through a sugar linkage such that F and F' are constituents of a first and a second polymeric chains; Y is the first polymeric chain having the structure $FN_iF\text{-}[N_jF'N_iF'\text{-}(N_jFN_iFF)_p\text{-}]_q$; N' is a nucleotide having a modified heterocyclic nitrogenous base having a linking group thereon for covalently attaching the first polymeric chain Y to N'; F and F' can be the identical fluorophores or different fluorophores capable of producing distinguishable fluorescent signals at two distinguishable wavelengths; i,j and k are integers ranging from 2 to 7; p is 0 or 1; and m are integers ranging from 1 to 3; q is an integer ranging from 0 to 5; and n is an integer ranging from 1 to 5.

In another aspect, the present invention provides a method for labeling a component present in a liquid comprising: (1) adding to the liquid a labeled oligonucleotide of the present invention and (2) labeling the component by covalently attaching the labeled oligonucleotide to amine, hydroxy groups and sulfydryl groups on the component under suitable reaction conditions.

In another aspect, the present invention provides oligonucleotides labeled with fluorophores which are covalently bound to the modified heterocyclic nitrogenous base of the oligonucleotide through a linking group.

In another aspect, the present invention provides an oligonucleotide primer comprising a labeled oligonucleotide.

In another aspect, the present invention provides a labeled primer comprising, an oligo dT sequence for hybridization to the poly A tail of mRNA.

In another aspect, the present invention provides a method for using the labeled primers and/or oligonucleotides of the invention to prepare fluorescently labeled nucleic acid molecules.

In another aspect, the present invention provides a set of labeled oligonucleotide primers for sequencing DNA molecules, wherein the set comprises a first, second, third and fourth labeled oligonucleotide primer; wherein the first through fourth labeled oligonucleotides are capable of generating four different pairs of distinguishable fluorescent signals at four to eight distinguishable wavelengths.

In another aspect, the present invention provides a method for sequencing a DNA molecule comprising the steps of: (a) generating four different sets of differently sized polynucleotide fragment terminating at a different base are generated (with the members of each set terminating at the same base) using a set of labeled primers; (b) combining said primer extension products; (c) separating said primer extension products; (d) producing an electropherogram by plotting the intensity of emitted light at four pairs of distinguishable wavelengths as a function of time as each primer extension product passes relative to a detector; and (e) determining the sequence of said DNA molecule.

In another aspect, the present invention provides a set of two labeled oligonucleotide primers, the set comprising a first and second fluorescently labeled oligonucleotide primer; wherein the first and second labeled oligonucleotides both are capable of generating one to two distinguishable fluorescence signals at one to two distinguishable wavelengths.

In another aspect, the present invention provides a method for generating fluorescently labeled cDNA molecules comprising: (1) obtaining a RNA sample from a physiological source and using the RNA sample as a template in a primer extension reaction, wherein the RNA sample is a total RNA sample or a poly A RNA sample; (2) generating fluorescently labeled cDNA molecules by using the above described oligo dT primer. In another aspect, this method is accomplished in a single step.

In another aspect, the present invention provides a method for using fluorescently labeled cDNA molecules in determining the level or pattern of the expression of proteins encoded genes under study.

In another aspect, the present invention provides a kit for sequencing DNA molecules comprising a set of labeled oligonucleotide primers.

In another aspect, the present invention provides a kit for generating two populations of fluorescently labeled cDNA molecules from two physiological sources comprising a set of two fluorescently labeled oligo dT primers. Such kits may further comprise one or more additional reagents, such as dNTPs, one or more fluorescently labeled dNTPs, which are labeled with the same fluorophore as in the fluorescently labeled primers, enzymes, such as reverse transcriptases, DNA polymerases, and the like, various buffer mediums, e.g. hybridization and washing buffers, prefabricated microarrays, and the like.

DETAILED DESCRIPTION OF THE INVENTION

Before the present invention is further described, it is to be understood that the invention is not limited to the particular embodiments of the invention described below, as variations of particular embodiments may be made and still fall within the scope of the appended claims. It is also to be understood that the terminology employed is for the purpose of describing particular embodiments, and is not intended to be limiting.

It must be noted that as used in this specification and the claims, the singular forms "a", "an", and "the" include plural reference unless the context clearly dictates otherwise.

One aspect of the present invention relates to a novel class of labeled oligonucleotides comprising a plurality of fluorophores of one or more types that are embedded in the backbone of the labeled oligonucleotides.

The term "label" refers to a molecule that, when attached covalently or non-covalently to a target molecule, renders the target molecule detectable using known detection means.

As used above and throughout this application, "a plurality" means two or more.

As used herein, the term "polymeric chain" refers to any one of a number of natural and synthetic compounds of usually high molecular weight consisting of up to millions of repeated linked units, each a relatively light and simple molecule. Particular examples of polymeric chains include polynucleotide chains including DNA (e.g., oligonucleotides), RNA, and cDNA.

The term "fluorophore" refers to a molecule that emits light when irradiated with radiation of a particular wavelength or wavelength range.

The term "embedded", as used herein, means that each of fluorophores of a labeled oligonucleotide is covalently bound to one or more non-fluorescent chemical moieties (e.g., nucleotides) of the labeled oligonucleotide.

The term "linking group" refers to a reactive group capable of reacting with a complementarily functional group to form a covalent linkage. The reactive group can be varied widely. Exemplary reactive groups include but are not limited to mono- or di-halogen substituted pyridine, isothiocyanate, isocyanate, monochlorotriazine, dichlorotriazine, mono- or di-halogen substituted diazine, maleimide, aziridine, sulfonyl halide, acid halide, succinimidyl ester, active carboxylate, hydroxysuccinimide ester, hydroxysulfosuccinimide ester, imido ester, hydrazine, axidonitrophenyl, azide, hydroxy, amine, sulthydryl, and the like. The linking group can be aliphatic, alicyclic, aromatic or heterocyclic, or combination thereof. The linking group can be rigid or flexible.

In another aspect, the present invention relates to an oligonucleotide molecule labeled with a plurality of fluorophores of one or more types embedded in the backbone of said oligonucleotide, wherein at least one of said fluorophores is not located at either the 3' or 5' terminus of said oligonucleotide.

In another aspect, the present invention relates to a labeled oligonucleotide having the general structure shown in Formula I immediately below Formula I wherein N is a nucleotide unit; F and F' are respectively a first and a second fluorophore which is covalently attached to the sugar moiety of N through a sugar linkage such that the first and second fluorophores are constituents of a polymeric chain. i and j are integers ranging from 2 to 7; s is 0 or 1; and r is an integer ranging from 1 to 5.

Nucleotide units N in the labeled oligonucleotides of the invention include (a) nucleotides comprising sugar moieties and heterocyclic nitrogenous bases found in naturally occurring DNA and RNA, e.g. adenine, cytosine, guanine, thymine and uracil either with or without modification on heterocyclic nitrogenous rings (modified heterocyclic nitrogenous base); and (b) nucleotide analogs comprising heterocyclic nitrogenous base analogs, modified sugar moieties, phosphate analogs, or combination thereof (Scheit, Nucleotide Analogs, John Wiley, N.Y., 1980, herein incorporated by reference in its entirety).

Modified heterocyclic nitrogenous bases refer to heterocyclic nitrogenous bases having modification on heterocyclic rings. Generally, heterocyclic nitrogenous base analogs can comprise inosine, xanthine, hypoxanthine, 1,2-diaminopurine, 2,6-diaminopurine, pseudouridine, C-5-propyne, isocytosine, isoguanine, 2-thiopyrimidine, and the like.

Sugar moieties will generally be five member rings, e.g. pentose, or six member rings, e.g. hexose, with five member rings such as pentose being preferred. Modified sugar moieties are sugar moieties having modification on the five or six member rings. Exemplary modified sugar moieties include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro and bromo.

Generally, phosphate analogs comprise analogs of phosphate where the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present.

The term "sugar linkage" refers to a covalent linkage between a sugar and another sugar or other molecules. A number of sugar linkage may be employed. Exemplary sugar linkages include phosphodiester, phosphorothiate, methylene(methylimino) (MMI), methophosphonate, phosphoramadite, guanidine, and the like (See Matteucci & Wagner, Nature (1996) Supp 84:20–22., which is incorporated herein by reference in its entirety). Generally, the sugar linkage is formed by the reaction of a linking group and a complementary functional group. In a preferred embodiment, the sugar linkage is a phosphodiester.

F and F' can be any fluorophore. Examples of fluorophores suitable with the compositions and methods of the invention include, any conventional label used for detection of oligonucleotides, including, without limitation, fluorescent dyes chosen from the group consisting of xanthenes (e.g., fluoresceins and eosins), rhodamines, benzimidazoles, ethidiums, propidiums, anthracyclines, mithramycins, acridines, actinomycins, merocyanines, coumarins, pyrenes, chrysenes, stilbenes, anthracenes, naphthalenes, salicylic acids, benzofurans, indodicarbocyanines, fluorescamine, and psoralen. F and F' may have two linking groups. The linking group preferably is a hydroxy group, amine, hydroxysuccinimide ester, or phosphoramidite. The fluorophore label of the invention can be added during synthesis of the oligonucleotide or added subsequently.

F and F' can be identical fluorophores or different fluorophores capable of producing distinguishable fluorescent signals at two distinguishable wavelengths. A fluorescent signal generally comprises the measured intensity of emitted light at around a specific wavelength, normally at which a fluorophore emits light maximally upon excitation. The term "distinguishable fluorescent signals," as used herein, refers to two fluorescent signals differing in the intensity of emitted light, wavelengths at which emission is maximum, or combination thereof. For example, two intensities of emitted light at the same wavelength are either distinguishable or the same, or two intensities of emitted light at two distinguishable wavelength are either distinguishable or the same. The term "distinguishable intensities" refers to intensities which can be distinguished using conventional measurement techniques. In a preferred embodiment, distinguishable intensities refer to two intensities having a ratio of from 1.5 to 5, preferably from 2 to 3. The term "distinguishable wavelengths" refers to two different wavelengths, having emission maxima that are not the same wavelength, as determinable by conventional measurement techniques. The difference between two distinguishable wavelength is variable, primarily depending on the emission band half-width of two fluorophores. In one preferred embodiment, the emission maxima of two distinguishable wavelengths differ by at least 25 nm, more preferably by at least 30 nm.

In a preferred embodiment, F and F' are fluorescent cyanine-type dyes. Many structures and synthetic procedures of cyanine-type dyes are available. Specific cyanine-type dyes having specific excitation and emission wavelengths can be prepared by varying the number of methine groups or by modifying cyanine ring structures. For example, Cy3™ and Cy5™ are two cyanine derivatives that have 3 and 5 methine groups in the conjugated polymethine linkage between two cyanine rings. Cyanine-type dyes with different charges can be made by the modification on the rings. Cyanine-type dyes have been synthesized that absorb and emit in a region of the spectrum ranging from 400 nm to near 1100 nm. Synthesis of a variety of cyanine-type dyes with linking groups has been disclosed in U.S. patents (U.S. Pat. No. 5,627,027; U.S. Pat. No. 4,337,063; US Pat. No. 4,404,289; U.S. Pat. No. 4,405,711; U.S. Pat. No. 4,414,325, British Patent 1,529,202; all of which are herein incorporated by reference in their entireties). Amidites of fluorophores (including Cy3 and Cy5) may be purchased commercially from sources including Glen Research (Sterling, VA) and Amersham. Amidites of these fluorophores can be used as starting materials to prepare the labeled oligonucleotides of the present invention, where the fluorophores are attached to nucleotide units through a phosphodiester sugar linkage.

Another aspect of the present invention relates to a branched labeled oligonucleotide comprising fluorophores embedded in the backbone of a oligonucleotide having a first polymeric chain and a second polymeric chain. A general structure of the branched polymeric labeled oligonucleotides is shown in Formula II immediately below Formula II wherein N is a nucleotide unit; F and F' are respectively a first and a second fluorophore which iscovalently attached to the sugar moiety of N through a sugar linkage such that F and F' are constituents of a first and a second polymeric chains; Y is the first polymeric chain having the structure $FN_iF\text{-}[N_jF'N_iF\text{-}(N_jFN_iF)p]q$; N' is a nucleotide having a modified heterocyclic nitrogenous base having a linking group thereon for covalently attaching the first polymeric chain Y to N'; i,j and k are integers ranging from 2 to 7; p is 0 or 1; and m are integers ranging from 1 to 3; q is an integer ranging from 0 to 5; and n is an integer ranging from 1 to 5.

The nucleotide N' in the branched labeled oligonucleotides of the invention can be, for example,: (a) nucleotides (e.g., adenine, cytosine, guanine, thyrnine and uracil) having a modified heterocyclic nitrogenous base, wherein the ring of heterocyclic nitrogenous base is modified to contain a linking group and (b) nucleotide analogs having a modified heterocyclic nitrogenous base or a modified heterocyclic nitrogenous base analog, wherein the ring of heterocyclic nitrogenous base or analogue thereof is modified to contain a linking group. In an aspect of the invention the first polymeric chain Y can be covalently attached to N' through a linking group on F at the 3' end or 5' end.

One embodiment of the linear and branched labeled oligonucleotides of the present invention is that a plurality of fluorophores are embedded in the backbone of the labels. In one aspect of the invention, the labeled oligonucleotide comprises between about 2 and about 10 fluorophores, more preferably between about 2 and about 5. The labeled oligonucleotides with such structural characteristics offer considerable advantages in enhancing the detecting sensitivity over an oligonucleotide labeled with a single fluorophore label or a fluorescent ET label having a donor and acceptor fluorophores. First, fluorophores in the labeled oligonucleotides of the invention are confined in a well defined position and separated from each other by nucleotide units and sugar linkages. Such an approach can minimize the self-quenching of fluorescence in labeled oligonucleotides. Thus, labeled Ioligonucleotides of the invention can have higher fluorescence per molecule than those labels of the prior art. Second, by adjusting the number of fluorophores in the labeled oligonucleotides shown in Formula I & U of the present invention, not only the fluorescence per label molecule but also the absorbance at a specific excitation wavelength can be increased. Third, the labeled oligonucleotides of the present invention minimize effects on the hybridization of the labeled primers to targeted nucleotide sequences as the number of the nucleotide units is much shorter than that of labeled oligonucleotide primers and fluorophores are embedded in the backbone of the labeled oligonucleotides. By employing the labeled oligonucleotides of the invention in the labeling of oligonucleotide primers, the sensitivity of DNA detection in hybridization assays can be increased.

Another embodiment of the present invention is that the labeled oligonucleotides can comprise a plurality of two or more types of fluorophores. In a preferred embodiment, two fluorophores, a first fluorophore F and a second fluorophore F', are spatially arranged in a way such that they can provide two strong, distinguishable fluorescent signals at two distinguishable wavelength upon excitation at a common wavelength. In the labeled oligonucleotides of the present invention, one fluorophore can be an energy donor, for example the first fluorophore F, which absorbs energy upon excitation at an excitation wavelength within its absorption spectrum and emits energy at a wavelength within its emission spectrum, and the other fluorophore can be an energy acceptor, for example the second fluorophore F', which accepts the energy emitted by the donor at a wavelength within the absorption spectrum of the acceptor and emits energy at a wavelength within the emission spectrum of the acceptor. The wavelength of the absorption maximum of the donor fluorophore is shorter than the wavelength of the absorption maximum of the acceptor fluorophore; and the wavelength of the emission maximum of the donor fluorophore is shorter than the wavelength of the emission maximum of the acceptor fluorophore. It is known that the energy transfer efficiency depends on the several factors such as spectral overlap between the emission spectrum of the donor and the absorption spectrum of the acceptor, spatial distance between donor and acceptor fluorophores, relative orientation of donor and acceptor fluorophore, quantum yield of the donor and excited state lifetime of the donor. By appropriately selecting the donor and acceptor fluorophores and by changing the spatial distance through variation of the number j of nucleotide units in Formula I or through variation of m and j of nucleotide units in Formula II, energy can transfer efficiently from the donor fluorophore to the acceptor fluorophore in the labeled oligonucleotides of the present invention to make the labeled oligonucleotide having a large excitation-emission wavelength shifts or Stokes shift. As used herein the term Stokes shift refers to the absolute difference in nanometers between the shortest wavelength of the absorption maximums of the fluorophores and the longest wavelength of the emission maximums of the fluorophores. Thus, a set of labeled oligonucleotides of the present invention are capable of being excited at a common wavelength but emitting light at the distinguishable wavelengths. Furthermore, because of the spatial arrangement of the first and second fluorophores in the backbone of the labeled oligonucleotides of the present invention, one fluorophore at the 5' end of the linear polymeric chain in Formula I and one F or F' at the unattached end of the first polymeric chain and one F' at the 5' end or 3' end of the second polymeric chain in Formula II may not participate in energy transfer. The fluorescence emission characteristics of F and F' can be preserved. Therefore, the labeled oligonucleotide of the present invention can provide two strong, distinguishable fluorescent signals at two distinguishable wavelengths upon excitation at a common wavelength.

In addition to the embodiment of the invention which includes a donor fluorophore and a first acceptor fluorophore, the labeled oligonucleotide may further have a second acceptor fluorophore. The wavelength of the emission maximum of the second acceptor fluorophore is longer than the wavelength of the emission maximum of the first acceptor fluorophore, and a portion of the emission spectrum of the first acceptor fluorophore overlaps a portion of the absorption spectrum of the second acceptor fluorophore. Energy can be transferred consecutively from the donor fluorophore to the first acceptor fluorophore to the second fluorophore, so that a larger Stokes shift can be achieved with the labeled oligonucleotides of the invention. Examples of appropriate fluorophore pairs include hexachlorofluoroscein-Cy3 and hexachlorofluoroscein-TAMRA. For a further discussion of fluorescent resonance energy transfer see J. R. Lakowicz, "Principles of Fluorescence Spectroscopy", Second Edition, Kluwer Academic/Plenum Publishers, (June 1999), which is herein incorporated by reference in its entirety.

An advantage of using the labeled oligonucleotides of the present invention over using traditional fluorescent ET labels in enhancing the sensitivity and accuracy of identifying/quantifying components of mixtures are: (1) that they can provide strong fluorescent signals at different wavelengths upon excitation at one to two wavelengths, since a plurality of a pair of energy transfer fluorophores can be embedded in a well designed spatial order in the backbone of the labeled oligonucleotides; (2) that they can generate two strong, distinguishable fluorescent signals at a pair of distinguishable wavelengths because of the spatial arrangement of two types of fluorophores. Such labeled oligonucleotides can be monitored either at one of two distinguishable wavelengths or simultaneously at two distinguishable wavelengths. When two-wavelength mode is used in identifying/quantifying a to-be-tested component in a sample, one fluorescent signal at one wavelength can be served as an internal reference for the other fluorescent signal at the other wavelength, so that the effects of instrument noise on the reliability of detection can be minimized significantly.

Another aspect of the present invention relates to the use of the labeled oligonucleotides of the invention. Since the labeled oligonucleotides of the invention can have a variety of linking groups which are covalently reactive under suitable reaction conditions with amine (-NH2), hydroxy (—OH), and sulfhydryl (—SHSH—) groups, they can be used in any processes for which current labeled oligonucleotides are being used. Examples include labeling biological materials such as antibodies, antigens, avidin, proteins, peptides, derivatized nucleotides, carbohydrates, lipids, biological cells, bacteria, viruses, blood cells, tissue cells, hormones, lympbokines, trace biological molecules, toxins and drugs. Fluorescent dyes can also be used to label non-biological materials such as soluble polymers and polymeric particles, glass, monomers, drugs, surfaces and particles. The component being labeled can be in a mixture including other materials. The mixture, in which the labeling reaction occurs, can be a liquid mixture, particularly a water mixture. The detection step can occur with the mixture in a liquid or dry condition, such as a microscope slide.

The labeled oligonucleotide of the present invention can be used to selectively label one or more components in a liquid, especially an aqueous liquid. The labeled component can then be detected, for example, by spectrophotometric and/or luminescence methods. Alternately, the labeled component can then be used to stain a second component for which it has a strong affinity, and the presence of the second component is then detected by optical or luminescence methods. In this case, a labeled oligonucleotide can be reacted with an amine, hydroxy or sulfhydryl group on the labeled component For example, a labeled component can be an antibody and the stained component for which it has a strong affinity can be a biological cell, an antigen or a hapten, or a biological cell or particle containing said antigen or hapten. In another example, a labeled component is avidin and the stained component can be biotinylated materials. Also, lectins conjugated with the labeled oligonucleotides of the present invention can be used to detect and quantify specific carbohydrate groups. In addition, the labeled oligonucleotides of the present invention can be attached to fragments of DNA or RNA. The labeled fragments of DNA or RNA can then be used as fluorescent hybridization probes to identify the presence and quantity of specific complementary nucleotide sequences in samples of DNA or RNA. Also, the dye can be attached to a hormore or ligand (such as a hormore, protein, peptide, lymphokine, metabolite) which in turn can be attached to a receptor.

Another aspect of the present invention relates to a method for labeling a component selected from the group consisting of antibodies, antigens, avidin, proteins, peptides, derivatized nucleotides, carbohydrates, lipids, biological cells, bacteria, viruses, blood cells, tissue cells, hormones, lympholines, trace biological molecules, toxins and drugs in a liquid comprising: (1) adding to the liquid a labeled oligonucleotide of the present invention and (2) labeling the component by covalently attaching the labeled oligonucleotide with amine, hydroxy groups, and sulfydryl groups, on the component under suitable reaction conditions. If the labeled component is an antibody, DNA fragment, hormone, lymphokine, or drug, the labeled component can be used to identify the presence of a second component to which it binds, and then the second component can be detected and/or quantified.

Labeled oligonucleotides of the invention can be used in applications where at least two components of a sample or mixture of components are to be distinguishably detected. In such applications, the sample will be combined with a first and a second labeled oligonucleotides of the present invention under conditions in which at least two of the components of the sample if present at all will be labeled with first and second labeled oligonucleotides, where the first and second labeled oligonucleotides are capable of producing two to four distinguishable fluorescent signals at two to four distinguishable wavelengths, a first fluorescent signal or a first pair of distinguishable fluorescent signals being attributed to the first labeled oligonucleotide and a second fluorescent signal or a second pair of distinguishable fluorescent signals being attributable to the second labeled oligonucleotide. A first component of the sample is labeled with a first label and a second component of the sample is labeled with a second label. Thus, the labeled first and second components can be distinguishably detected by monitoring two to four distinguishable fluorescent signals from the labeled components at two to flour distinguishable wavelengths.

Labeled oligonucleotides of the invention find particular use in polynucleotide sequencing applications. Nearly all currently available automated DNA sequencing machines are based on the enzymatic chain termination method of Sanger (Sanger et al., Proc. Natl. Acad. Sci. U.S.A. 74: 5463–5467 (1977), which is incorporated herein by reference in its entirety). According to Sanger's sequencing method, one starts with a purified DNA template of interest and an oligonucleotide primer complementary to a specific site on the template strand. For each of the 4 bases (A, C, G, T), an enzymatic extension reaction is carried out in which DNA polymerase synthesizes a population of labeled single-stranded fragments, each having a common origin and each terminating with a known base. In such applications, four different labeled oligonucleotides of the present invention can be used in labeling primers used in four enzymatic extension reactions, wherein each labeled oligonucleotides comprise a plurality of two different types of fluorophores and are capable of producing a pair of distinguishable fluorescent signals at four different pairs of distinguishable wavelengths selected from a group consisting of 4 to 8 different distinguishable wavelengths. Using methods known in the art, a first set of primer extension products all ending in A will be generated by using primers labeled with a first labeled oligonucleotides. Second, third and fourth sets of primer extension products terminating in G, C and T will be also be enzymatically produced. The four different sets of primer extension products will then be combined and size separated, usually in an electrophoretic medium. The separated fragments will then be moved relative to a detector (where usually either the fragments or the detector will be stationary). The intensity of emitted light at four to eight distinguishable wavelengths from each labeled fragment as it passes relative to the detector will be plotted as a function of time, i.e. an electropherogram or raw data will be produced. Each peak in the electropherogram will correspond to a particular type of primer extension product (i.e. A, G, C or T), where one of four pairs of distinguishable fluorescent signals at one of four pairs of distinguishable wavelengths can be found under each peak. To determine the DNA sequence, the electropherogram will be read, with each pair of distinguishable fluorescent signals related to one of the four different bases in the polynucleotide. By using an internal reference, sequences can be called with a higher accuracy in automatic DNA sequencing and human involvement in base calling and editing may be minimized.

The present invention in another aspect provides a set of four fluorescently labeled oligonucleotide primers for sequencing a DNA molecule, said set comprising one or more of the following: (a) a first fluorescently labeled oligonucleotide primer comprising a first labeled oligonucleotide capable of providing a first pair of distinguishable fluorescent signals at a first pair of distinguishable wavelengths; (b) a second fluorescently labeled oligonucleotide primer comprising a second labeled oligonucleotide capable of providing a second pair of distinguishable fluorescent signals at a second pair of distinguishable wavelengths; (c) a third fluorescently labeled oligonucleotide primer comprising a third labeled oligonucleotide capable of providing distinguishable fluorescent signals at a third pair of distinguishable wavelengths; or (d) a fourth fluorescently labeled oligonucleotide primer comprising a fourth labeled oligonucleotide capable of providing a fourth pair of distinguishable fluorescent signals at a fourth pair of distinguishable wavelengths; wherein said first through fourth labeled oligonucleotides comprise a plurality of two types of fluorophores which are embedded in the backbone of the labeled oligonucleotides and are capable of generating said first through fourth pairs of distinguishable fluorescent signals at four different pairs of distinguishable wavelengths selected from four to eight distinguishable wavelengths.

The present invention in another aspect provides a method for sequencing a DNA molecule, said method comprising the steps of: (a) enzymatically producing a first set of primer extension products terminating in adenine using a first fluorescently labeled oligonucleotide primer comprising a first labeled oligonucleotide capable of providing a first pair of distinguishable fluorescent signals at a first pair of distinguishable wavelengths; (b) enzymatically producing a second set of primer extension products terminating in guanine using a second fluorescently labeled oligonucleotide primer comprising a second labeled oligonucleotide capable of providing a second pair of distinguishable fluorescent signals at a second pair of distinguishable wavelengths; (c) enzymatically producing a third set of primer extension products terminating in thymine using a third fluorescently labeled oligonucleotide primer comprising a third labeled oligonucleotide capable of providing distinguishable fluorescent signals at a third pair of distinguishable wavelengths; (d) enzymatically producing a fourth set of primer extension products terminating in cytosine using a fourth fluorescently labeled oligonucleotide primer comprising a fourth labeled oligonucleotide capable of providing a fourth pair of distinguishable fluorescent signals at a fourth pair of distinguishable wavelengths; (e) combining said four sets of primer extension products; (f) separating said primer extension products with a electrophoresis means; (g) producing an electropherogram by plotting the intensity of emitted light at four pairs of wavelengths as a function of time as each primer extension product passes relative to a detector; and (h) determining the sequence of said DNA molecule by one of four different pairs of distinguishable fluorescent signals under each peak in said electropherogram; wherein said first through fourth labeled oligonucleotides comprise a plurality of two types of fluorophores which are embedded in the backbone of the labeled oligonucleotides and are capable of generating said first through fourth pairs of distinguishable fluorescent signals at four different pairs of distinguishable wavelengths selected from four to eight distinguishable wavelengths.

A DNA sequencing method of the present invention can be adopted directly in the current automatic DNA sequencing technology using four-color (or four distinguishable wavelengths: first, second, third and fourth). For example, a set of four distinct labeled oligonucleotides comprises: a first labeled oligonucleotide capable of providing a first and a second distinguishable fluorescent signals at a first and a second wavelengths; a second labeled oligonucleotide capable of providing a second and a third distinguishable fluorescent signals at a second and a third wavelengths; a third labeled oligonucleotide capable of providing a third and a fourth distinguishable fluorescent signals at a third and a fourth wavelengths; a fourth labeled oligonucleotide capable of providing a first and a fourth distinguishable fluorescent signals at a first and a fourth wavelengths. By using such set of labeled oligonucleotides in four-color DNA sequencing, each peak in the electropherogram will still correspond to a particular type of primer extension product (i.e. A, G, C or T). However, there are two distinguishable fluorescent signals found under each peak. This sequencing method can be called as a twin fur-color sequencing, because it is equivalent to that a DNA sequencing has been done twice under identical conditions. The reliability of this sequencing method can be much higher than current. four-color sequencing method.

It is understood that the twin four-color sequencing method of the present invention can be carried out using labeled oligonucleotides which are widely used in enzymatic DNA sequencing. Currently, in many automated DNA sequencing four populations of fluorescently labeled single-stranded fragments, each having a common origin and each terminating with a known base, are labeled with different labeled oligonucleotides, which are attached either to a primer (e.g. Smith et al Nature, 321: 674–679 (1987)) or to the base of a terminal dideoxynucleotide (e.g. Prober et al Science, 238: 336341 (1987); Prober et al, Section II, Meth. Enzymol., 155: 51–334 (1987), all of which are herein incorporated by reference in their entireties). In the method of the present invention, both labeled oligonucleotideing technologies can be used together to obtain the four populations of fluorescently labeled single-stranded fragments, using a set of labeled oligonucleotides comprising (1) a first labeled oligonucleotide capable of generating a first fluorescent signal at a first wavelength; (2) a second labeled oligonucleotide capable of generating a second fluorescent signal at a second wavelength; (3) a third labeled oligonucleotide capable of generating a third fluorescent signal at a third wavelength; and (4) a fourth labeled oligonucleotide capable of generating a fourth fluorescent signal at a fourth wavelength, wherein the first through fourth fluorescent signals are distinguishable and the first through fourth wavelengths are distinguishable. For example, a first enzynatic extension reaction is carried out in which DNA polymerase synthesizes a first population of fluorescently labeled single-stranded fragments using a first primer, each having a common origin and each terminating with the base adenine, wherein the first primer is labeled with the first labeled oligonucleotide and terminal nucleotides are labeled with the second labeled oligonucleotide; a second enzymatic extension reaction is carried out in which DNA polymerase synthesizes a second population of fluorescently labeled single-stranded fragments using a second primer, each having a common origin and each terminating with the base guanine, wherein the second primer is labeled with the second labeled oligonucleotide and terminal nucleotides are labeled with the third labeled oligonucleotide; a third enzymatic extension reaction is carried out in which DNA polymerase synthesizes a third population of fluorescently labeled single-stranded fragments using a third primer, each having a common origin and each terminating with the base cytosine, wherein the third primer is labeled with the third labeled oligonucleotide and terminal nucleotides are labeled with the fourth labeled oligonucleotide; and a fourth enzymatic extension reaction is carried out in which D:NA polymerase synthesizes a fourth population of fluorescently labeled single-stranded fragments using a fourth primer, each having a common origin and each terminating with the base thymine, wherein the fourth primer is labeled with the first labeled oligonucleotide and terminal nucleotides are labeled with the fourth. The four populations of primer extension products will then be combined and size separated, usually in an electrophoretic medium. The separated fragments will then be moved relative to a detector (where usually either the fragments or the detector will be stationary). The intensity of emitted light at four distinguishable wavelengths from each labeled fragment as it passes relative to the detector will be plotted as a function of time, i.e. an electropherogram or raw data will be produced. Where the first and second distinguishable fluorescent signals at the first and second wavelengths are found under a peak in the electropherogram, the peak corresponds to a primer extension product of base adenine; where the second and third distinguishable fluorescent signals at the second and third wavelengths are found under a peak in the electropherogram, the peak corresponds to a primer extension product of base guanine; where the third and fourth distinguishable fluorescent signals at the third and fourth wavelengths are found under a peak in the electropherogram, the peak corresponds to a primer extension product of base cytosine; and where the first and fourth distinguishable fluorescent signals at the first and fourth wavelengths are found under a peak in the electropherogram, the peak corresponds to a primer extension product of base thymine.

Another aspect of the present invention relates to a method for generating fluorescently labeled cDNA molecules, comprising the steps of (1) obtaining a RNA sample from a physiological source, wherein the RNA sample is a total RNA sample or a poly A RNA sample; (2) contacting the RNA sample with a pre-labeled oligonucleotide primer and requisite reagents under conditions sufficient for reverse transcription of the mRNA in the sample, wherein the oligonucleotide primer is pre-labeled with a labeled oligonucleotide of the invention; (3) generating the fluorescently labeled cDNA molecules.

Another aspect of the present invention relates to a method for generating fluorescently labeled cDNA molecules, comprising the steps of (1) obtaining a RNA sample from a physiological source; (2) contacting the RNA sample with a pre-labeled oligonucleotide primer and requisite reagents under conditions sufficient for reverse transcription of the mRNA in the sample, wherein the oligonucleotide primer is labeled with a labeled oligonucleotide of the invention, wherein the requisite reagents comprise a mixture of fluorescently labeled dNTPs and unlabeled dNTPs, wherein the fluorescently labeled dNTPs are labeled with a fluorophore which is identical to those contained in the labeled oligonucleotide in the labeling of the primer; (3) generating the fluorescently labeled cDNA probes.

The RNA sample is a total RNA sample or a poly A RNA sample, preferably a total RNA sample.

Preferably, the pre-labeled oligonucleotide primer used to prime cDNA synthesis comprises an "oligo dT sequence" and a labeled oligonucleotide of the invention linked at the 5' end of the oligo dT sequence. "Oligo-dT sequence" is relatively short chains of deoxythymidine units, e.g. from 10 to 100 bases, preferably from 10 to 50 bases, more preferably from 12 to 30 bases.

The pre-labeled oligonucleotide primers of the present invention may be prepared using any suitable method, such as, for example, the known phosphodiester and phosphodiester methods, automated embodiments thereof, or any of the commercially available DNA synthesis devices. e.g. those available from Applied Biosystems, Inc. (850-T Lincoln Center Drive, Foster City, CA 94404). In one such automated embodiment, phosphoramidites are used as starting materials and may be synthesized as described by Beaucage et al., Tetrahedron Letters 22: 1859–1962 (1981), herein incorporated by reference in its entirety. In a preferred embodiment, the pre-labeled oligonucleotide primer is synthesized on a modified solid support.

The physiological source of total RNA will typically be eukaryotic, with physiological sources of interest including sources derived from single celled organisms such as yeast and multicellular organisms, including plants and animals, where the physiological sources from multicellular organisms may be derived from particular organs or tissues of the multicellular organism, or from isolated cells derived therefrom. Thus, the physiological sources may be different cells from different organisms of the same species and from different tissue types, including normal and diseased tissue types. Methods of isolating total RNA from cells, tissues, organs or whole organisms are known to those of skill in the art and are described in Maniatis et al., Molecular Cloning: A Laboratory Manual (Cold Spring Harbor Press)(1989), herein incorporated by reference in its entirety. Poly A RNA can be isolated from total RNA by methods known to those of skill in the art.

Requisite reagents contacted with the primer and RNAs are known to those of skill in the art and will generally include at least an enzyme having reverse transcriptase activity and dNTPs in the an appropriate buffer medium.

A variety of enzymes, usually DNA polymerases, possessing reverse transcriptase activity can be used for cDNA synthesis. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776, human T-cell leukemia virus type I (HTLV-I), bovine leukemia virus (BLV), Rous sarcoma virus (RSV), human immunodeficiency virus (HIV) and Thermus aquaticus (Taq) or Thermus thermophilus (Tth) as described in U.S. Pat. No. 5,322,770. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like.

The various dNTPs and buffer medium necessary for cDNA synthesis through reverse transcription of the primed mRNA may be purchased commercially from various sources, where such sources include Amnersham, Boehringer-Mannheim, Clontech, Life Technologies, Sigma. Buffer mediums suitable for cDNA synthesis will usually comprise buffering agents, such as Tris-HCl, HEPES-KOH, etc.; salts containing monovalent ions, such as KCl, NaCl, etc.; salts containing divalent cations like $MgCl_2$, Mg(OAc) etc.; and additional reagents such as reducing agents, e.g. DDT, detergents, albumin and the like. The conditions of the reagent mixture will be selected to promote efficient first strand synthesis. Typically the primers will first be combined with the total RNA sample at an elevated temperature, usually ranging from 50° C. to 95° C., followed by a reduction in temperature to a range between about 0 to 60° C., to ensure specific annealing of the primers to their corresponding mRNAs in the sample. Following this annealing step, the primed mRNAs are then combined with dNTPs and reverse transcriptase under conditions sufficient to promote reverse transcription and first strand cDNA synthesis of the primed RNAs. By using appropriate types of reagents, all of the reagents can be combined at once if the activity of the polymerase can be postponed or timed to start after annealing of the primer to the mRNA.

The order in which the reagents are combined may be modified as desired. One protocol that may be used involves the combination of all reagents except for the reverse transcriptase on ice, then adding the reverse transcriptase and mixing at around 4° C. Following mixing, the temperature of the reaction mixture is raised to 37° C., followed by incubation for a period of time sufficient for first strand cDNA primer extension product to form, usually about 1 hour.

The fluorescently labeled cDNA molecules find use in comparing the characteristic mRNA profiles of different physiological sources and identifying differences in the mRNA profiles between different physiological source. Comparison of the mRNA profiles of two or more physiological sources finds particular use in methods of identifying differential gene expression in two physiological samples, such as cells or tissues derived from the same or different individual organisms, where the tissues may represent different diseased or normal states, different organ or tissue types, etc.

The fluorescently labeled cDNA molecules generated from the plurality of physiological sources may be compared in a number of different ways. One may compare the fluorescently labeled cDNA molecules from each source by separately resolving the fluorescently labeled cDNA molecules from each source under substantially identical electrophoretic conditions to yield an electrophoretic pattern of resolved bands for each of the different populations of fluorescently labeled cDNA molecules. The resultant electrophoretic patterns can then be resolved to identify differences between the fluorescently labeled cDNA populations, which differences can then be attributed to differences in the mRNA profiles of the each of the physiological sources, where such differences can, in turn, be attributed to difference in gene expression (Liang & Pardee, Science 257: 967 (1992), herein incorporated by reference in its entirety). Conveniently, electrophoretic separation under identical electrophoretic conditions can be achieved by running the labeled nucleic acids derived from each physiological source of interest in separate, side by side lanes on a slab gel. Automated electrophoretic machines as described in U.S. Pat. Nos. 5,410,412; 5,275,710; 5,217,591; and 5,104,512, the disclosures of which are herein incorporated by references, may be employed to resolve the labeled nucleic acids.

In a modification of the above, where a first population of cDNA molecules from a first physiological source is labeled with a first labeled oligonucleotide of the invention and a second population of cDNA molecules from a second physiological source is labeled with a second labeled oligonucleotide of the invention, where the first and second labeled oligonucleotides are capable of producing distinguishable fluorescent signals at two or more distinguishable wavelengths, the opportunity arises to resolve the two populations of fluorescently labeled cDNA molecules in the same electrophoretic medium, e.g. the same column or in the same lane of a slab, thereby ensuring that the nucleic acids are resolved under identical electrophoretic conditions. The labeled first and second populations of fluorescently labeled cDNA molecules can be distinguishably detected by determining distinguishable fluorescent signals. The resultant electrophoretic patterns can then be resolved to identify differences between the fluorescently labeled cDNA populations, which differences can then be attributed to differences in the MRNA profiles of the each of the physiological sources, where such differences can, in turn, be attributed to difference in gene expression.

Most preferably, one may hybridize the fluorescently labeled cDNA molecules as probes to predefined arrays of polymeric molecules stably associated with the surface of a substrate, where the polymeric molecules as gene targets are capable of sequence specific base pair hybridization to complementary labeled cDNA probes. A variety of different arrays which may be used are known m the art.

In analyzing the differences in the population of fluorescently labeled cDNA probes generated from two or more physiological sources using the arrays described above, each population of fluorescently labeled cDNA probes are separately contacted to identical target arrays under hybridization conditions, preferably under stringent hybridization conditions, such that the labeled cDNA probes hybridize to their complementary targets on the substrate surface. Suitable hybridization conditions are well known to those of skill in the art.

As with the electrophoretic analysis, where all of the cDNA probes comprise the same label, different arrays will be employed for each physiological source. Alternatively, where the labeled oligonucleotides of the cDNA probes are different and distinguishable for each of the different physiological sources being assayed, the opportunity arises to use the same array at the same time for each of the different probe populations.

In one preferred embodiment of assays using microarrays, two populations of cDNA probes are generated from two physiological sources and labeled separately with a first and a second labeled oligonucleotides, where the first labeled oligonucleotide can provide a first distinguishable fluorescent signal or a first pair of distinguishable fluorescent signals at a first wavelength or a first pair of distinguishable wavelengths and the second labeled oligonucleotides are capable of generating a second distinguishable fluorescent signal or a second pair of distinguishable fluorescent signals at a second wavelength or a second pair of distinguishable wavelengths, wherein the first and second wavelengths are distinguishable and the first and second pairs of distinguishable wavelengths are any combination of two of four distinguishable wavelengths. The two populations of fluorescently labeled cDNA probes are hybridized simultaneously to gene targets on a microarray. Following hybridization, non-hybridized labeled cDNA probes are removed from the support surface, conveniently by washing. A variety of wash solutions are known to those of skill in the art and may be used. The resultant hybridization patterns of two populations of labeled cDNA probes are detected or visualized by separately determining distinguishable fluorescent signals at two to four distinguishable wavelengths.

Following detection or visualization, the hybridization patterns may be compared to identify differences between the patterns. Where arrays in which each of the different targets corresponds to a known gene are employed, any discrepancies can be related to a differential expression level of a particular gene in the physiological sources being compared.

The present invention in another aspect provides a set of two fluorescently labeled oligonucleotide primers for generating fluorescent cDNA molecules. Such set comprises a first fluorescently labeled oligonucleotide primer comprising a first labeled oligonucleotide attached covalently to the 5' end the first primer; and a second fluorescently labeled oligonucleotide primer comprising a second labeled oligonucleotide attached covalently to the 5' end of the second primer; wherein the first and second labeled oligonucleotides comprise a plurality of one to two types of fluorophores embedded in the backbone of the labeled oligonucleotides and are capable of generating two to four distinguishable fluorescent signals at two to four distinguishable wavelengths.

Also provided in the present invention are kits for use in carrying out the subject methods, e.g. generating populations of fluorescently labeled cDNA molecules, performing differential gene expression analysis and the like. The kits according to the subject invention include at least a set of oligonucleotide primers that are labeled with a plurality of labeled oligonucleotides and employed to generate a plurality of populations of fluorescently labeled cDNA molecules from a plurality of physiological sources, where the labeled oligonuclectides are capable of generating distinguishable fluorescent signals. Of particular interest are kits comprising a set of oligonucleotide primers comprising an oligo dT sequence, where the labeled oligonucleotides are linked at the 5' end of the oligo dT sequence, where the oligo dT sequence is a chain of deoxythymidine units from 10 to 100 bases, preferably from 10 to 50 bases, more preferably from 12 to 30 bases.

The kits of the invention may further comprise one or more additional reagents employed the various methods, such as dNTPs, one or more fluorescently labeled dNTPs, which are labeled with the same fluorophore as in the fluorescently labeled primers, enzymes, such as reverse transcriptases, DNA polymerases, and the like, various buffer mediums, e.g. hybridization and washing buffers, prefabricated microarrays, and the like.

The following examples are provided to better elucidate the practice of the present invention and should not be interpreted in any was to limit the scope of the present invention. Those skilled in the art will recognize that various modifications, substitutions, etc., can be made to the labeled oligonucleotides and methods described herein while not departing from the spirit and scope of the present invention.

Example 1

Synthesis of the Fluorescently Labeled Oligonucleotide Primers

CATA: 5' Cy3-TTTT-Cy3-TTT TTT TTT TTT TTT TTT TTT 3'(SEQ ID NO: 1)

CATB. 5' Cy5-TTTT-Cy5-TTT TTT TTT TTT TTT TTT 3'(SEQ ID NO: 2)

CAT1: 5' Cy3-TTT-Cy3-TTT-Cy3-TTT TTT TTT TTT TT 3'(SEQ ID NO: 3)

CAT2: 5' Cy5-TTT-Cy5-TTT-Cy5-TTT TTT TTT TTT TT 3'(SEQ ID NO: 4)

CATAb: 5' Cy3-TTT-Cy3-TTT TTT TTT TTT TTT TTT 3'(SEQ ID NO: 5) C≡CH—O—$(CH_2)_3$ NH—(CO)—$(CH_2)_2$-Cy3-TTT-Cy3

Synthesis of the fluorescently labeled oligonucleotide primers. CATA, CATB, CAT1, and CAT2, are carried out in a series of steps. First, oligo $(dT)_{21}$ (SEQ ID NO: 6) and d(T)$_{14}$ (SEQ ID NO: 7) are chemically synthesized on solid support as described by Matteucci et al., J. Am. Chem. Soc. 103: 3185 (1981), which is incorporated herein by reference in its entirety. Deoxythymidine diethylphosphoramidites are used as starting materials and may be synthesized as described by Beaucage et al., Tetrahedron Letters 22: 1859–1962 (1981), which is incorporated herein by reference in its entirety. Second, a first fluorophore, having two hydoxypropyl groups as linking groups, is attached to the 5' end of the oligo (dT)2z (SEQ ID NO: 6) or oligo d(T)$_{14}$ (SEQ ID NO: 7) through a phosphodiester bond. The starting material for this reaction step is N,N-dimethylaminophosphoramidite of the fluorophore of choice with one of two hydroxy groups protected by a dimethoxytrityl group. Third, three or four deoxythymidine diethylphosphoramidites are attached sequentially to the 5' end of extending oligomers. Fourth, step 2 reaction is repeated to add a second fluorophore. Step 3 and step 4 are repeated until a fluorescently labeled primer having a desired number of fluorophores is obtained. After cleavage from the solid support, the oligonucleotide primers are evaporated to dryness under vacuum (0.5 mm of Hg) and then purified by standard HPLC methods. The fluorescently labeled oligonucleotide primers are then dissolved in 1× TE buffer (pH7.0) and stored at −20' C. freezer.

Synthesis of the oligonucleotide primer labeled with a branched labeled oligonucleotide, CATAb, are carried out in a series of steps. For example, first, a long oligomer 5' Cy3-TT'T-Cy3-(T)$_{21}$ 3'(SEQ ID NO: 5) and a short oligomer 5' Cy3-TTT-Cy3 3' are chemically synthesized on solid support as described above. A modified base T' is introduced in the long oligomer by the use of 5'-dimethoxytrityl-5-[N-(trifluoroacetylarninopropoxy)-1-propynyl)]-2'-deoxyuridine, 3'-[(2-cyanoehtyl)-(N,N-diisopropyl)]-phosphoramidite which has a protected primary amine linking arm at the C-position. The Cy3 at the 5' end of the short oligomer contains a N-hydroxysuccinimide ester linking arm at the N-1' position. The short oligomer is attached to the primary amine group on the T' by reacting with the N-hydroxysuccinimde active ester group on the Cy3 at the 5' end of the short oligomer in a sodium carbonate/bicarbonate solution at pH 9.2.

Labeled oligonucleotides of the invention may be prepared by methods well known to those of ordinary skill in the art, e.g. the phosphoramidite, phosphodiester, phosphodiester, phosphite and H-phosphonate methods, each of which are commonly known in the field of oligonucleotide chemistry and molecular biology. For example, the β-cyanoethyl phosphoramidite method is described in U.S. Pat. No. 4,458,066 issued to Caruthers, et al., entitled "Process for Preparing Polynucleotides," which is incorporated herein by reference. These methods are amenable to use with commercially available DNA synthesizers (e.g., ABI 380B DNA synthesizer) or other equipment. For an example of such an instrument see U.S. Pat. No. 5,472,672, which is incorporated herein by reference in its entirety.

Example 2
Generation of Fluorescent cDNA Probes from Total RNA or Poly A RNA

The fluorescent cDNA probes were generated using 1× kits or 4×kits. Each kit consists of 4 reaction tubes, A3, A5, B3 and B5, each of which contains pre-mixed reagents. The contents of the two kits are listed in Table 1. A3 & B3 are used to generate Cy3 probes and A5 & B5 to generate Cy5 probes. One 1× kit can be used to generate cDNA probes only for one microarray hybridization experiment and one 4×kit to generate cDNA probes for 4 microarray hybridization experiments. Four to six micrograms of total RNA or 200–400 nanograms of poly-A RNA were needed to generate probes for each hybridization assay. The procedure for preparing fluorescent cDNA probes using 1× kits is described below. The same procedure was used in the preparation of fluorescent cDNA probes using 4×kits.

TABLE 1

|  | 1x | 4x |
|---|---|---|
| A3 | | |
| Primer CATA (1.0 μg/μl): | 3 μl | 12 μl |
| Incyte Cy3 Yeast Control RNA: | 5 μl | 20 μl |
| A5 | | |
| Primer CATB (1.0 μg/μl): | 3 μl | 12 μl |
| Incyte Cy5 Yeast Control: | 5 μl | 20 μl |
| B3 | | |
| 5x M-MLV buffer | 6 μl | 24 μl |
| 0.1 M DTT | 3 μl | 12 μl |
| sdNTP (dATP, dTTP, dGTp, 2.0 mM each, dCTP 1.0 mM) | 3 μl | 12 μl |
| Cy3-dCTP (Amersham Pharmacia) | 3 μl | 12 μl |
| B5 | | |
| 5x M-MLV buffer | 6 μl | 24 μl |
| 0.1 M DTT | 3 μl | 12 μl |
| sdNTP (dATP, dTTP, dGTP, 2.0 mM each, dCTP 1.0 mM) | 3 μl | 12 μl |
| Cy5-dCTP (Amersham Pharmacia) | 3 μl | 12 μl |

4 μl of to-be-labeled RNA samples (about 4 to 6 micrograms of total RNA or about 200 to 400 nanograms of poly-A RNA) was added into each of two tubes A3 and A5 respectively. The samples were mixed thoroughly with reagents in A3 and A5 by pipetting and then spun briefly in a bench-top microcentrifuge. A3 and A5 containing the samples were heated at 70° C. for 8 minutes in a water bath. A3 and A5 were spun briefly and kept at room temperature (in the dark) for 8 to 10 minutes. Contents in A3 were then transferred to a tube B3 on ice and contents in A5 to a tube B5 on ice. Then, 1.5 μof RNase inhibitor and 1.5 μl of reverse transcriptase (M-MLV) were added to each of the two tubes B3 and B5. The reagents were mixed by pipetting and incubated at 37° C. for 90 min. The reverse transcription was then stopped by heating at 80° C. for 10 minutes. The fluorescent cDNA probes were generated in the presence of dNTPs including dCTP labeled with Cy3 in B3 or dCTP labeled with Cy5 in B5. Two populations of fluorescent cDNA probes generated with different fluorophores (Cy3 and Cy5) were then combined for subsequent purification and concentration of fluorescent cDNA probes. 2.5 μl of Rnase mix (Rnase, DNAse free, Boehringer Mannhem : RNase H, Life Technologies, =3:1) was added to the combined solution after purification and concentration. The resultant solution was incubated at 37° C. for 20 minutes to remove RNA. The fluorescent cDNA probes were then purified by using one spin column (Chroma Spin TE-200, Clontech, Calif.) per 1× kit by following the manufacturer's recommendation. The volume from the STE-200 column was measured and brought to 90 μl with water or TE in a 1.5-ml microcentrifuge tube. 1 micrograms of glycogen, 60 μl of 5.0 M ammonium acetate NH$_4$OAc, 400 μl of cold 100% alcohol were then added to the purified cDNA probes. The mixture was vortexed and centrifuged at >16000 g at 4° C. for 30 min. The supernatant was carefully removed and the remaining cDNA probes were resuspend by heating at 65° C. for 5 minutes in 28 μl of heated resuspension/hybridization buffer (Incyte). At this point, the cDNA probes contained both Cy3-labeled cDNA generated from one RNA sample and Cy5-labeled cDNA generated from another RNA sample.

It has been found that the level of fluorescent background noise depended on the concentration of primers in kits used in preparation of cDNA probes. Preferably, the concentration of primers in 1× or 4× kits was 0.5 μg/μl, half of the concentration shown in Table 1. By using such kits with lower primer concentration in preparation of cDNA probes, the level of fluorescent background noise in hybridization assays was lower. However, the data shown in Examples 3 and 4 were obtained using kits shown in Table 1 in preparation of cDNA probes.

Example 3

Microarray-based Gene Expression Assays

Custom Gene Expression Microarrays (GEMs) with approximately 10000 elements (cDNA clones from either corn or soybean) were fabricated and provided by Incyte Microarray Division (Fremont. Calif.). The spin-column purified cDNA probes, containing both CATA-labeled cDNA probes generated from one cell population and CATB-labeled cDNA probes generated from another cell population, were resuspended in the hybridization buffer consisting of 5× SSC and 0.2% SDS (Incyte Genomics, Palo Alto, Calif.). 24 μl of the cDNA probe solution was hybridized to a GEM for 6 hours at 65' C. in a custom-built hybridization chamber. The GEM was then washed for 10 minutes at 45° C. in 0.2× SSC and 0.2% SDS; and then rinsed in a 0.2× SSC and 0.2% SDS at room temperature for 10 minutes. The GEM was spun dry and scanned with a confocal laser array scanner (Axon Instrument); and the intensities of Cy3 and Cy5 fluorescent signals at each microarray element (cDNA clone), which, in theory, should be positively proportional to the expression level of that element (gene), were measured and then analyzed in GEM-TOOL (Incyte Genomics, Palo Alto, Calif.). The ratio of the two fluorescent intensities was calculated and used as an indicator of the relative gene expression level in the two cell populations tested.

Example 4

Characterization of Fluorescently-Labeled cDNA Probes (1) Length of Fluorescently labeled cDNA Probes The length of fluorescently labeled cDNA probes prepared from a single biological materials source has been characterized according to the following procedure. 3 μl of each probe and 3 μl of glycerol were mixed and electrophoresed in a 1.5 to 2.0% agarose gel (SeaKem Gold, FMC BioProducts, Rockland, Maine) without ethidium bromide in a Hoefer HE33 apparatus in 1× TAE buffer at 80 V for 40 minutes. RNA ladder 0.16 to 1.77 kb, Gibco/Life Technologies (1 microgram) 20, was mixed with 3 μl of formaldehyde, 5 μl of formamide, and 1 μl of 10× TAE. After heating at 65° C. for 10 minutes, 0.3 μl of ethidium bromide and 5 μl of glycerol were added and loaded along with the cDNA probes. The length of the labeled cDNA probes were assessed with the help of FluorImager 595 (for Cy3 fluorescence) and STORM 860 (for Cy5 fluorescence), both from Molecular Dynamics (Sunnyvale, Calif.).

Figure 1:
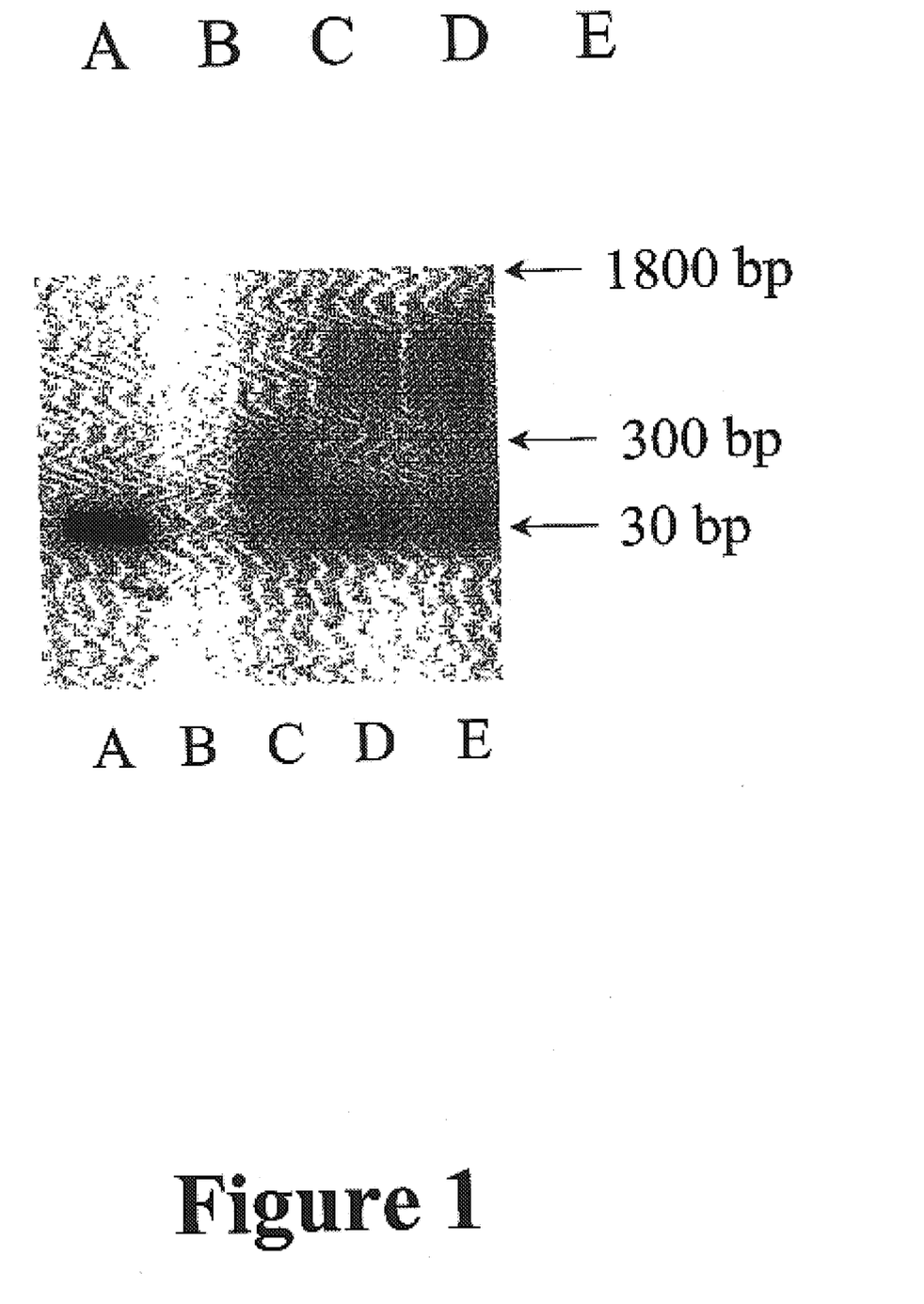
FIG. 1 Comparison of length of probes generated by the method of the present invention with those generated by the GEMBRIGHT method (Incyte Genomics, Palo Alto. Calif.).

FIG. 1 shows the experimental results of the characterization of the length of fluorescently labeled cDNA probes. Lane A was loaded with primers pre-labeled with the labeled oligonucleotides (CATA and CATB) of the present invention. Lane B was a blank lane. Lane C was loaded with fluorescently labeled cDNA probes, which were generated from a poly A RNA sample isolated from the biological source using the GEMBRIGHT method (Incyte Genomics, Palo Alto, Calif.). Lane D was loaded with fluorescently labeled cDNA probes, which were generated from a poly A RNA sample isolated from the biological source by the use of the pre-labeled primer and method of the present invention. Lane E was loaded with fluorescently labeled cDNA probes, which were generated from a total RNA sample isolated from the biological source using the pre-labeled primers and method of the present invention. Both cDNA probe samples in Lane C and D were generated from the same poly A RNA sample. The length of the cDNA probes generated according to the method of the present invention was around 1000 bps, whereas the length of the cDNA probes generated using Incyte's the GEMBRIGHT method (Incyte Genomics, Palo Alto, Calif.) was around 150 bps (FIG. 1). Such results demonstrate that the method of present invention provides significant improvement in preparing cDNA probes over the prior art. (2) Enhancement of Hybridization Signals Parallel hybridization assays were carried out with cDNA probes, which were generated from the same poly A RNA sample using the fluorescently labeled primers and method of the present invention and the GEMBRIGHT method (Incyte Genomics, Palo Alto, Calif.), to assess if hybridization signals on microarrays can be enhanced by using the labeled oligonucleotides and the method of the present invention to generate fluorescent cDNA probes.

Poly A RNA sample isolated from corn or soybean leaves from a single seedling was divided into two parts. One part (200 nanograms) was used to generate a first population of fluorescently labeled cDNA probes; and another 200 nanograms to generate a second population of fluorescently labeled cDNA probes. These two population of fluorescently labeled cDNA probes were then combined for probe purification and concentration. The mixture of fluorescently labeled cDNA probes was then resuspended in 24 μl of hybridization buffer and applied to corn or soybean cDNAs GEMs for hybridization as described in Example 3.

An average intensity of observed hybridization signals was obtained by averaging intensities of all Cy3 or Cy5 fluorescent signals of individual elements. The results are shown in Table 2. In average, the hybridization signals on microarrays were at least 2 fold stronger for cDNA probes generated by using the labeled oligonucleotides and cDNA probe preparation method of the present invention than by using the GEMBRIGHT method (Incyte Genomics, Palo Alto, Calif.).

TABLE 2

| | GEMBRIGHT (Incyte Genomics, Palo Alto. CA) | | Method of the Invention | |
| --- | --- | --- | --- | --- |
| Labeled oligonucleotide | Cy3 | Cy5 | CATA | CATB |
| Average hybridization signal (RNA source: corn leaves) | 603 | 677 | 1992 | 2002 |
| Average hybridization signal (RNA source: soybean leaves) | 713 | 689 | 5881 | 5560 |

(3) Comparison of Hybridization Assay Performance on Microarrays of cDNA Probes Prepared from Total RNA with Those from Poly RNA Experiments have been carried out to compare the performance of cDNA probes prepared from a total RNA sample and from a poly RNA sample using labeled oligonucleotide of the present invention, as described below.

Total RNA samples were extracted, respectively, from the leaves at $2^{nd}$ node and $5^{th}$ node of a single soybean plant. Poly A RNAs were then isolated from their respective total RNA samples. The total RNA and poly A RNA from the leaves at 2$^{nd}$ node were labeled with CATA label comprising two Cy3 fluorophores with a 1× kit; and similarly, the total RNA and poly A RNA from the leaves at 5$^{th}$ node were labeled with CATB label comprising two Cy5 fluorophores. The Cy3-labeled (2$^{nd}$ node) and Cy5-labeled (5$^{th}$ node) cDNA probes generated from total RNA samples were co-hybridized to soybean cDNA GEMs; and the Cy3-labeled (2$^{nd}$ node) and Cy5-labeled (5$^{th}$ node) cDNA probes generated from poly A RNA samples were co-hybridized to the same soybean cDNA GEMs. The results were summarized in Table 3. It has been found that the cDNA probes generated directly from total RNA samples are slightly brighter than those from poly A RNA samples. The cDNA probes prepared from poly A RNA samples identified a total of 12 genes (excluding control sequences) out of 10176 elements (genes) on the soybean cDNA GEMs with either up-regulated or down-regulated greater than 2.0 folds in the two leaves compared. 1 1 out of these 12 differentially expressed genes were also identified by the probes directly generated from total A RNA samples. Furthermore, the cDNA probes directly generated from the total RNA samples identified more differentially expressed genes (a total of 72). This result demonstrates that the fluorescently labeled cDNA probes are preferably prepared directly from total RNA samples.

TABLE 3

Total RNA vs Poly A RNA*

|  | Total RNA | poly-A RNA |
| --- | --- | --- |
| Average hybridization signal (Cy3) | 6953 | 5965 |
| Average hybridization signal (Cy5) | 6462 | 6283 |

TABLE 3-continued

Total RNA vs Poly A RNA*

|  | Total RNA | poly-A RNA |
| --- | --- | --- |
| Average fluorescence background (Cy3) | 287 | 242 |
| Average fluorescence background (Cy5) | 234 | 186 |
| Amounts of RNA sample for cDNA probe preparation | 4–6 µg | 200–400 ng |
| Differentially expressed genes | 72 | 12 |

*Probes: both total and poly-A RNAs
Cy3  soybean A3244 leaf at 2$^{nd}$ node of plant at V4 stage
Cy5  soybean A3244 leaf at 5$^{th}$ node of plant at V4 stage It is clear from the experimental data that labeled oligonucleotides of the present invention offer higher fluorescence signals and therefore can enhance the sensitivity and reliability of characterization of differential expression of genes expressed in a relatively low level.

It is evident from the above results and discussion that the cDNA probes preparation method of the present invention provide for a number of advantages. Small amount of starting materials is required by the method of the invention. Artificial errors occurred during MRNA isolation are likely minimized. The length of cDNA probes generated by using the method of the invention is around 1000 bps and hybridization assays can be performed under more optimal conditions. The cDNA probes, generated by using the labeled oligonucleotides of the invention according to the method of the invention, can produce higher fluorescent hybridization signals and increase the sensitivity and reliability of microarray assays for characterizing differential expression of genes.

What is claimed is:

1. An oligonucleotide molecule labeled with a plurality of fluorophores of one or more types embedded in the backbone of said oligonucleotide, wherein at least one of said fluorophores is not located at either the 3' or 5' terminus of said oligonucleotide.

2. The labeled oligonucleotide of claim 1, wherein said oligonucleotide is a branched oligonucleotide.

3. The labeled oligonucleotide of claim 1, wherein said oligonucleotide is an unbranched oligonucleotide.

4. The labeled oligonucleotide of claim 1, having a structure selected from the group consisting of:

(a) $F\text{-}[N_iF\text{-}(N_jF'N_iF'N_jF)_s]_r$ wherein N is a nucleotide unit; F and F' are respectively a first and a second fluorophore which is attached to a sugar moiety of N through a sugar linkage such that the first and second fluorophores are constituents of a polymeric chain; i and j are integers ranging from 2 to 7; s is 1; and r is an integer ranging from 1 to 5;

(b)

wherein N is a nucleotide unit; F and F' are respectively a first and a second fluorophore which is covalently attached to a sugar moiety of N through a sugar linkage such that Fs and F's are constituents of a first and a second polymeric chain; Y is the first polymeric chain having the structure $FN_iF\text{-}[N_jF'N_iF'\text{---}$ $(N_jFN_iF)_p]_q$; N' is a nucleotide having a modified heterocyclic nitrogenous base having a linking group thereon for covalently attaching the first polymeric chain Y to N'; i,j and k are integers ranging from 2 to 7; p is 0 or 1; and m are integers ranging from 1 to 3; q is an integer ranging from 0 to 5; and n is an integer ranging from 1 to 5; and (c) $F-[N_iF]_r$ wherein N is a nucleotide unit; F is a fluorophore which is attached to a sugar moiety of N through a sugar linkage such that the fluorophore is a constituent of a polymeric chain; i is an integer ranging from 2 to 7; and r is an integer ranging from 2 to 5.

5. The labeled oligonucleotide of claim 1, wherein the oligonucleotide sequence comprises an oligo dT sequence.

6. The labeled oligonucleotide of claim 5, wherein the oligo-dT sequence comprises between about 10 and about 50 deoxythymidine bases.

7. The labeled oligonucleotide of claim 1, wherein all of said fluorophores have the same structure.

8. The labeled oligonucleotide of claim 1, wherein all of said fluorophores do not have the same structure.

9. The labeled oligonucleotide of claim 8, wherein said fluorophores are capable of generating two distinguishable fluorescent signals at two distinguished wavelengths.

10. A set of labeled oligonucleotides with a plurality of fluorophores of one or more types embedded in the backbone of said oligonucleotides, wherein at least one of said fluorophores is not located at either the 3' or 5' terminus of said oligonucleotides.

11. The set of labeled oligonucleotides of claim 10, wherein said set comprises four labeled oligonucleotides, wherein the oligonucleotides do not have the same structure.

12. The set of labeled oligonucleotides of claim 11, wherein said set of labeled oligonucleotides is capable of being used for sequencing nucleic acid molecules.

13. The set of labeled oligonucleotides of claim 11, further comprising (1) a first labeled oligonucleotide capable of generating a first pair of distinguishable fluorescent signals at a first pair of two distinguishable wavelengths; (2) a second labeled oligonucleotide capable of generating a second pair of distinguishable fluorescent signals at a second pair of two distinguishable wavelengths; (3) a third labeled oligonucleotide capable of generating a third pair of distinguishable fluorescent signals at a third pair of two distinguishable wavelengths; (4) a fourth labeled oligonucleotide capable of generating a fourth pair of distinguishable fluorescent signals at a fourth pair of two distinguishable wavelengths; wherein, said first, second, third and fourth pairs of distinguishable fluorescent signals are different from each other; and said first, second, third and fourth pairs of distinguishable wavelengths are different from each other.

14. The set of labeled oligonucleotides of claim 10, wherein at least one of said labeled oligonucleotides have the structure selected from the group consisting of:

(a) $F-[N_iF-(N_jF'N_iF'N_jF)_s]_r$ wherein N is a nucleotide unit; F and F' are respectively a first and second fluorophore which is attached to the sugar moiety of N through a sugar linkage such that the first and second fluorophores are constituents of a polymeric chain; i and j are integers ranging from 2 to 7; s is 1; and r is an integer ranging from 1 to 5;

(b)

wherein N is a nucleotide unit; F and F' are respectively a first and second fluorophore which is covalently attached to a sugar moiety of N through a sugar linkage such that F and F' are constituents of a first and a second polymeric chain; Y is the first polymeric chain having the structure $FN_iF-[N_jF'N_iF'-(N_jFN_iF)_p]_q$; N' is a nucleotide having a modified heterocyclic nitrogenous base having a linking group thereon for covalently attaching the first polymeric chain Y to N'; i,j and k are integers ranging from 2 to 7; p is 0 or 1; and m are integers ranging from 1 to 3; q is an integer ranging from 0 to 5; and n is an integer ranging from 1 to 5; and (c) $F-[N_iF]_r$ wherein N is a nucleotide unit; F is a fluorophore which is attached to a sugar moiety of N through a sugar linkage such that the fluorophore is a constituent of a polymeric chain; i is an integer ranging from 2 to 7; and r is an integer ranging from 2 to 5.

15. The set of claim 13, wherein each of the first through fourth pairs of distinguishable wavelengths comprises a combination of two distinguishable wavelengths of a group of 4 to 8 distinguishable wavelengths.

16. The set of claim 13, wherein each of the first through fourth pairs of distinguishable wavelengths comprises a combination of two distinguishable wavelengths of a group of 4 distinguishable wavelengths.

17. The set of labeled oligonucleotides of claim 10, wherein said set comprises 2 different labeled oligonucleotides.

18. The set of claim 17, wherein any or all of said labeled oligonucleotides have the structure selected from the group consisting of:

(a) $F-[N_iF-(N_jF'N_iF'N_jF)_s]_r$ wherein N is a nucleotide unit; F and F' are respectively a first and second fluorophore each of which is covalently attached to a sugar moiety of N through a sugar linkage such that the first and second fluorophores are constituents of a polymeric chain; i and j are integers ranging from 2 to 7; s is 1; and r is an integer ranging from 1 to 5;

(b)

wherein N is a nucleotide unit; F and F' are respectively a first and a second fluorophores each of which is covalently attached to the sugar moiety of N through a sugar linkage such that Fs and F's are constituents of a first and a second polymeric chains; Y is the first polymeric chain having the structure $FN_iF-[N_jF'N_iF'-(N_jFN_iF)_p]_q$; N' is a nucleotide having a modified heterocyclic nitrogenous base having a linking group thereon for covalently attaching the first polymeric chain Y to N'; i,j and k are integers ranging from 2 to 7; p is 0 or 1; and m are integers ranging from 1 to 3; q is an integer ranging from 0 to 5; and n is an integer ranging from 1 to 5; and (c) $F-[N_iF]_r$ wherein N is a nucleotide unit; F is a fluorophore which is attached to a sugar moiety of N through a sugar linkage such that the fluorophore is a constituent of a polymeric chain; i is an integer ranging from 2 to 7; and r is an integer ranging from 2 to 5.

19. The set of labeled oligonucleotides of claim 17, wherein said wherein the oligonucleotide sequence comprises an oligo dT sequence.

20. The labeled oligonucleotide of claim 19, wherein the oligo-dT sequence comprises between about 10 and about 50 deoxythymidine bases.

21. The set of labeled oligonucleotides of claim 17, wherein said first fluorescent label is capable of generating a first and second fluorescent signal respectively at a first and a second distinguishable wavelength and said second fluorescent label is capable of generating a second and third fluorescent signal respectively at a second and a third distinguishable wavelength.

22. A kit for use in generating fluorescently labeled cDNA molecules from a RNA sample comprising an oligonucleotide molecule labeled with a plurality of fluorophores of one or more types embedded in the backbone of said oligonucleotide molecule, wherein at least one of said fluorophores is not located at either the 3' or 5' terminus of said oligonucleotide molecule.

23. The kit of claim 22, wherein said labeled oligonucleotide comprises a fluorescent label attached to the 5' end of the oligonucleotide primer, the labeled oligonucleotide having a structure selected from the group consisting of:

(a) $F\text{--}[N_iF\text{--}(N_jF'N_iF'N_jF)_s]_r$ wherein N is a nucleotide unit; F and F' are respectively a first and a second fluorophore which is covalently attached to the sugar moiety of N through a sugar linkage such that the first and second fluorophores are constituents of a polymeric chain; i and j are integers ranging from 2 to 7; s is 1; and r is an integer ranging from 1 to 5;

wherein N is a nucleotide unit; F and F' are respectively a first and a second fluorophore which is covalently attached to the sugar moiety of Ns through a sugar linkage such that F and F' are constituents of a first and a second polymeric chains; Y is the first polymeric chain having the structure $FN_iF\text{--}[N_jF'N_iF'\text{--}(N_jFN_iF)_p]_q$; N' is a nucleotide having a modified heterocyclic nitrogenous base having a linking group thereon for covalently attaching the first polymeric chain Y to N'; i,j and k are integers ranging from 2 to 7; p is 0 or 1; and m are integers ranging from 1 to 3; q is an integer ranging from 0 to 5; and n is an integer ranging from 1 to 5; and wherein N is a nucleotide unit; F is a fluorophore which is attached to a sugar moiety of N through a sugar linkage such that the fluorophore is a constituent of a polymeric chain; i is an integer ranging from 2 to 7; and r is an integer ranging from 2 to 5.

24. The kit of claim 22, wherein said kit further comprises a reverse transcriptase.

25. The kit of claim 22, wherein said kit further comprises deoxynucleotides.

26. The kit of claim 22, further comprising one or more of reverse transcription buffer, reverse transcriptase, dNTPs, PCR buffer, control RNA, glycogen, water and loading dye.

27. A kit capable of use for DNA sequencing, said kit comprising a first, second, third and fourth oligonucleotide labeled with a plurality of fluorophores of one or more types embedded in the backbone of said oligonucleotide, wherein at least one of said fluorophores is not located at either the 3' or 5' terminus of said oligonucleotide.

28. The kit of claim 27, further comprising (1) a first labeled oligonucleotide capable of generating a first pair of distinguishable fluorescent signals at a first pair of two distinguishable wavelengths; (2) a second labeled oligonucleotide capable of generating a second pair of distinguishable fluorescent signals at a second pair of two distinguishable wavelengths; (3) a third labeled oligonucleotide capable of generating a third pair of distinguishable fluorescent signals at a third pair of two distinguishable wavelengths; (4) a fourth labeled oligonucleotide capable of generating a fourth pair of distinguishable fluorescent signals at a fourth pair of two distinguishable wavelengths; wherein, said first, second, third and fourth pairs of distinguishable fluorescent signals are different from each other; and said first, second, third and fourth pairs of distinguishable wavelengths are different from each other.

29. The kit of claim 27, wherein said first, second, third and fourth labeled oligonucleotides have a structure selected from the group consisting of:

(a) $F\text{--}[N_iF\text{--}(N_jF'N_iF'N_jF)_s]_r$ wherein N is a nucleotide unit; F and F' are respectively a first and a second fluorophore which is covalently attached to the sugar moiety of N through a sugar linkage such that the first and second fluorophores are constituents of a polymeric chain; i and j are integers ranging from 2 to 7; s is 1; and r is an integer ranging from 1 to 5;

wherein N is a nucleotide unit; F and F' are respectively a first and a second fluorophore which is covalently attached to the sugar moiety of Ns through a sugar linkage such that F and F' are constituents of a first and a second polymeric chains; Y is the first polymeric chain having the structure $FN_iF\text{--}[N_jF'N_iF'\text{--}(N_jFN_iF)_p]_q$; N' is a nucleotide having a modified heterocyclic nitrogenous base having a linking group thereon for covalently attaching the first polymeric chain Y to N'; i,j and k are integers ranging from 2 to 7; p is 0 or 1; and m are integers ranging from 1 to 3; q is an integer ranging from 0 to 5; and n is an integer ranging from 1 to 5; and (c) $F\text{--}[N_jF]_r$ wherein N is a nucleotide unit; F is a fluorophore which is attached to a sugar moiety of N through a sugar linkage such that the fluorophore is a constituent of a polymeric chain; i is an integer ranging from 2 to 7; and r is an integer ranging from 2 to 5.

30. The kit of claim 28, wherein each of the first through fourth pairs of distinguishable wavelengths comprises a combination of two distinguishable wavelengths of a group of 4 to 8 distinguishable wavelengths.

31. The kit of claim 30, wherein each of the first through fourth pairs of distinguishable wavelengths comprises a combination of two distinguishable wavelengths of a group of 4 distinguishable wavelengths.

32. The kit of claim 28, wherein said kit further comprises polymerase.

33. The kit of claim 28, wherein said kit further comprises deoxynucleotides and dideoxynucleotides.

* * * * *

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      CATA oligonucleotide

<400> SEQUENCE: 1 ttttttttttt tttttttttt ttttt                                        25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      CATB oligonucleotide

<400> SEQUENCE: 2 ttttttttttt tttttttttt ttttt                                        25

<210> SEQ ID NO 3
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      CAT1 oligonucleotide

<400> SEQUENCE: 3
tttttttttt tttttttttt                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      CAT2 oligonucleotide

<400> SEQUENCE: 4
tttttttttt tttttttttt                                                   20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      CATAb oligonucleotide

<400> SEQUENCE: 5
tttttttttt tttttttttt tttt                                              24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      dT oligonucleotide

<400> SEQUENCE: 6
tttttttttt tttttttttt t                                                 21

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      dT oligonucleotide

<400> SEQUENCE: 7
tttttttttt tttt                                                         14
```